United States Patent [19]

Bauer et al.

[11] Patent Number: 5,848,177
[45] Date of Patent: Dec. 8, 1998

[54] METHOD AND SYSTEM FOR DETECTION OF BIOLOGICAL MATERIALS USING FRACTAL DIMENSIONS

[75] Inventors: Wolfgang W. Bauer, East Lansing; Charles D. Mackenzie, Eaton Rapids, both of Mich.

[73] Assignee: Board of Trustees operating Michigan State University, East Lansing, Mich.

[21] Appl. No.: 807,827

[22] Filed: Feb. 27, 1997

Related U.S. Application Data

[63] Continuation of Ser. No. 368,159, Dec. 29, 1994, abandoned.

[51] Int. Cl.$^6$ ..................................................... G06K 9/00
[52] U.S. Cl. ........................... 382/128; 382/133; 382/249
[58] Field of Search ..................................... 382/128, 133, 382/134, 286, 224, 249; 128/634

[56] References Cited

U.S. PATENT DOCUMENTS

| | | | |
|---|---|---|---|
| 4,097,845 | 6/1978 | Bacus | 382/134 |
| 4,207,554 | 6/1980 | Resnick et al. | 382/134 |
| 4,453,266 | 6/1984 | Bacus | 382/134 |
| 4,538,299 | 8/1985 | DeForest | 382/197 |
| 4,741,043 | 4/1988 | Bacus | 382/134 |
| 4,771,469 | 9/1988 | Wittenburg | 382/203 |
| 5,016,173 | 5/1991 | Kenet et al. | 382/128 |
| 5,065,447 | 11/1991 | Barnsley et al. | 382/249 |
| 5,099,521 | 3/1992 | Kosaka | 382/133 |
| 5,121,436 | 6/1992 | Kasadan et al. | 382/128 |
| 5,257,182 | 10/1993 | Luck et al. | 382/133 |
| 5,313,532 | 5/1994 | Harvey et al. | 382/15 |
| 5,526,258 | 6/1996 | Bacus | 364/413.1 |
| 5,555,889 | 9/1996 | Karagueuzian et al. | 128/705 |

FOREIGN PATENT DOCUMENTS 93 16442  8/1993  WIPO ..................................... 382/128

OTHER PUBLICATIONS

K.S. Birdi, Fractals in Chemistry, Geochemistry and Biophysics, pp. 1 to 10.

*Primary Examiner*—Joseph Mancuso
*Assistant Examiner*—Jayanti K. Patel
*Attorney, Agent, or Firm*—Ian C. McLeod

[57] ABSTRACT

A method and system for classification of biological materials is described. The system (100) includes a microscope (10), a digitizing camera (20) and a computer (30). The method includes the steps of capturing the digital image (40) of the biological material or cell (12) using the digitizing camera preferably through the microscope (10). The captured image is digitized and displayed on the computer screen (32). The digitized image is then enhanced using a grey level value thresholding process, a cluster recognition process and a boundary determination process. The resulting enhanced image (40C) is then used to determine the perimeter surface (40D) of the cell. The enhanced image is subjected to a box counting routine in which the number of boxes occupied by the perimeter surface is calculated for various different box sizes. The box counting calculations are plotted using a power-law analysis. Using a linear regression fit to the data points, a straight line is fit to the data points and used to determine the fractal dimension D of the cell. A histogram of the resulting fractal dimensions D for various cells in a sample can be produced. The image enhancing process and the fractal dimension analysis is preformed by software in the computer. The method and system is useful in analyzing large amounts of cells in order to differentiate between neoplastic and non-neoplastic human cells of a given type. Other organisms can be analyzed by the method.

28 Claims, 10 Drawing Sheets

METHOD AND SYSTEM FOR DETECTION OF BIOLOGICAL MATERIALS USING FRACTAL DIMENSIONS

This application is a continuation of application Ser. No. 08/368,159 filed on Dec. 29, 1994 now abandoned.

BACKGROUND OF THE INVENTION

(1) Field of the Invention

The present invention relates to a method and system for determining the size and shape of biological materials using fractals. In particular, the invention relates to a method and apparatus for determining the surface morphometry of the biological material. The image of the biological material is digitized into a computer and a series of processes are performed on the image. The enhanced image is then subjected to a box counting algorithm to produce data which represents the surface shape of the material. The resulting data is subjected to a power-law analysis in order to determine the fractal dimension of the material. The fractal dimension is then compared with a known fractal dimension for a similar biological material in order to classify the biological material. The invention is particularly useful to distinguish abnormal blood cells from normal blood cells such as to detect hairy cell leukemia and to define organisms such as amoebas. In general, neoplastic cells can be distinguished from normal cells using this method and system.

(2) Prior Art

The conventional method of detection of the characteristics of cells involves taking a biopsy or surface scraping, preparing the cells by either cytological or histological techniques for visual examination under a microscope. The examining specialist looks at the interior components (chromatin, nucleoli) of the cell nucleus, abnormalities in the nuclear membrane as well as the size and shape of the cell itself. Existent quantitative measures of cell characteristics having digital imaging are based on area alone and do not to any extent consider shape.

Systems and methods for using digital images to analyze biological material are well known in the prior art. Illustrative are U.S. Pat. Nos. 4,097,845 to Bacus; 4,741,043 to Bacus; 5,121,436 to Kasdan et al; 4,771,469 to Wittenburg; 5,099,521 to Kosaka; 5,313,532 to Harvey and 5,065,447 to Barnsley et al.

Bacus (U.S. Pat. No. 4,097,845) describes a system for distinguishing normal cells from abnormal cells in a red blood cell specimen. The cells are classified by their internal configuration or central pallors as well as their size, area and shape. The location of the cell image, the identification of the cell and feature extraction from the cell image are preformed using a scene segmentation technique to locate and define the cells and extract the summed density or hemoglobin feature, followed by a boundary procedure which defines the cell in the form of an octal chain code. The individual cells in the image are located by a scene analysis technique in which a raster scan is made of the digitized image to locate a pixel above a critical threshold and to preform a four neighbor analysis of adjacent pixel elements until all the neighbors above the threshold are located and the entire region of the cell is defined. The next step is boundary tracing which forms the octal chain code which provides size, roundness, irregularity, spicularity, elongation and central pallor features for use in the classification. The system determines the shape of the cell by dividing the number of permanent pixels squared by the area of the cell.

Bacus (U.S. Pat. No. 4,741,043) describes a system similar to that above for dynamically testing and evaluating cells, antigens or other materials taken from the human body. Image analysis using pattern recognition techniques is used to analyze and quantify the DNA in specimen cells. To obtain digital image data using grey level or optical density measurements, the specimen is first stained in order to mark the DNA of the cell. When using the system for red blood cell analysis, the specimen does not need to be stained.

Kasdan et al describes a method and apparatus for generating a plurality of parameters of an object in a field of view as determined in response to positional information representing the boundary of the object. The electrical image is segmented to form a plurality of different representations which are representations of a different parameter of the field of view. The imaging system of the invention comprises a video image processor, which receives analog video signals from a color camera. The color camera is optically attached to a fluorescent illuminator which is focused through a microscope and is directed at a stage. The video imaging processor communicates with a host computer and a full color monitor display device receives the output of the video image processor. The imaging system can be used to analyze biological specimens such as biopsy material or constituents of blood. The specimen is mounted on a slide and placed on the stage. A video image of the slide as taken by the color camera through the microscope is processed by the video image processor. The positional information representing the boundary of the object can be determine by using a greyscale thresholding process on the digitized image data. This positional information is used to trace locations in the various different representations of the electrical image in order to calculate the different parameters of the object.

Wittenburg describes a method of processing an object image in order to extract information on the shape of the object. The invention employs successively finer levels of analysis of segments of the object's boundary by an interactive process to determine the shape of the object. The first step of the method is the generation of a two-dimensional digital image representing the shape of the object. Next, a boundary encoding processor identifies the boundary points, encodes the boundary points and consecutively orders the boundary points. A subset of boundary points is then selected. The subset of points is the "convex hull" vertices and is used to partition the boundary into segments by using a n-sided polygon wherein each side of the polygon connects two of the points of the subset. The segments are either concave arcs (first kind) or convex arcs (second kind) which form a first level of the shape tree. In the next step, all concave arcs of the first level are further segmented into concave and convex arcs which form a second level of the shape tree. This process continues until there are no concave arcs in the last level.

Kosaka shows a method and apparatus for processing cell images in which various cell image parameters relating to a number of cells, such as cumulative chromaticity information, chromaticity histograms, cumulative gradient information and gradient histograms can be obtained in one frame cycle from edge detection information relating to the cells. The processing method comprises the steps of capturing a cell image by image pickup means, storing the captured image data as an original image data, binarizing the image data upon identifying a background portion and cell image portions contained in the original image data, deriving cell edge detection information for each pixel from the binarized image data, tracing cell edges in order to obtain edge points of the cells by referring to the edge detection information and deriving various cell image parameters by referring results of the edge tracing. Characterized cell identification codes are derived when the edge tracing is performed. The cell information codes identify each edge point to indicate which edge point belongs to which cell and indicate which side of the edge point is exterior to the cell. The cell identification code is used when deriving the cell image parameters. The cell identification code is also used to determine whether each pixel is an edge on a starting point side of a cell as seen in a pixel-by-pixel scanning direction. When it is determined that the pixel is an edge on the starting point side, the cell number read from the cell identification code is latched and the image data of each pixel is totaled, cell number by cell number. If it is determined that the pixel is an edge on the end point side, the cell number is unlatched.

Harvey describes a method of recognizing a pattern within an image which consists of locating the pattern within the image, classifying the pattern to produce a spectrum and comparing the spectrum with spectrums of known cells. The classification channel includes edge detectors and also gross size detectors for detecting the gross size of a pattern within a portion of the image. Classification of the cells is done by selecting a single cell and enlarging the cell to a scale that fills an entire 175×175 pixel window within the image. The image is presented to the system and results in a spectrum which is classified by classifying as one mode of a first category. The spectrum is based on the array of subwindows each 7×7 pixels which tile the windows. The resulting spectrum for each cell in the image is compared to a sample known spectrums.

Barnsley et al describes a method for processing digital data which includes dividing stored image data into domain blocks and range blocks, subjecting the range block to a process to obtain mapped range blocks and matching the domain blocks with the most similar mapped range blocks. The resulting address of the range block and the processes performed on the range block are combined to form an identification used to identify the associate domain blocks. The resulting list of identifications for all the domain blocks is a fractal transform which constitutes a compressed representation of the input image.

There remains a need however for a quantitative method and system for classifying biological materials such as cells using a fractal dimension which represents the perimeter of the surface of the material to quickly and accurately classify the biological material.

OBJECTS

The object of the present invention is to provide a method and system for quick and accurate quantitative identification of abnormal cells in a biological material such as hairy cell leukemia cells in a blood sample. Further, it is an object of the present invention to provide a method and system for distinguishing neoplastic cells from normal cells. Still further, it is an object of the present invention to provide a method and system for quantifying the surface morphometry of a cell for use in identifying the cell. Further, it is an object of the present invention to provide a method and system for classifying organisms such as amoeba. Still further, it is an object of the present invention to provide a method and system for analyzing a large number of cells in a sample and selecting relevant and interesting cells based on the surface morphometry of the cells for visual re-examination by the user. Furthermore, it is an object of the present invention to provide a method and system which represents the surface of the sample cell as a fractal and uses a box counting method combined with the power-law to determine the fractal dimension of the cell which is then compared with the fractal dimension of known cells in order to classify the sample cell. Finally, it is an object of the present invention to provide a method and system to quickly and accurately determine the existence of hairy cell leukemia in a blood sample by analyzing a large quantity of cells without the need for subsequent visual re-examination by the user.

BRIEF DESCRIPTION OF THE DRAWINGS

The following FIG. 1 shows the system used for the digital image processing and the quantitative classification of the biological material. FIGS. 2 and 4 to 6 show the different stages of image processing for one single white human blood cell affected by hairy-cell leukemia. The individual FIGS. 2 and 4 to 6 show reproductions of the screen images generated by image processing software developed for this invention. They are shown at one quarter of the true resolution.

FIG. 1 is a schematic representation of the image capturing and processing system 100 showing the microscope 10, the digitizing camera 20, the computer 30 and the digitized image 40 of the cell 12.

FIG. 2 is a digitized computer image 40 showing a hairy cell leukemia affected white human blood cell 12. This image 40 was obtained using an electron microscope 10 (FIG. 1).

FIG. 3 is a computer screen 32 showing the grey level value distribution of pixels in FIG. 2. The long vertical grey line indicates the grey level value threshold (=80) used for generating FIG. 4.

FIG. 4 is a digitized black and white image 40A of the cell 12 of FIG. 2 after application of grey level value threshold declination to enhance contrast.

FIG. 5 is a digitized black and white image 40B of the cell 12 of FIG. 2 after execution of the cluster-recognition and the cluster-elimination algorithms. Clusters containing less than 300 pixels were eliminated by reversing their black/white value and thus incorporating them into the surrounding cluster.

FIG. 6 is a computer generated image 40C of the cell 12 of FIG. 2 showing the perimeter surface 40D of the image-enhanced cell 12.

FIG. 7 is a pictorial representation of the fractal box counting method for resolutions (l=0, 1, 2 and 3).

FIG. 8 is a graph showing the result of a fractal box counting algorithm on the image 40C of the surface of the cell 12 as shown in FIG. 6. The graph is the logarithm of the number of boxes N(l), touched by the perimeter surface 40D, as a function of the resolution l, where $2^{-l}$ is the sidelength s of an individual box. The straight line is a linear regression fit to the data points between l=2 and l=7, corresponding to a fractal dimension of D=1.34.

FIG. 9 is a histogram showing a comparison of the number distribution of fractal dimensions D of individual cells 12 for cell samples from four different persons. Persons 1 and 3 were diagnosed with hairy cell leukemia using independent methods, persons 2 and 4 were healthy. Only persons 1 and 3 have cells 12 with fractal dimensions D larger than 1.28 (dotted vertical line). The dashed histograms and numbers in brackets for persons 2 and 4 indicate the distributions for healthy lymphocytes only.

FIG. 10 is a flow chart showing the steps of the method preformed by the computer software.

DESCRIPTION OF PREFERRED EMBODIMENTS

Figure 1:
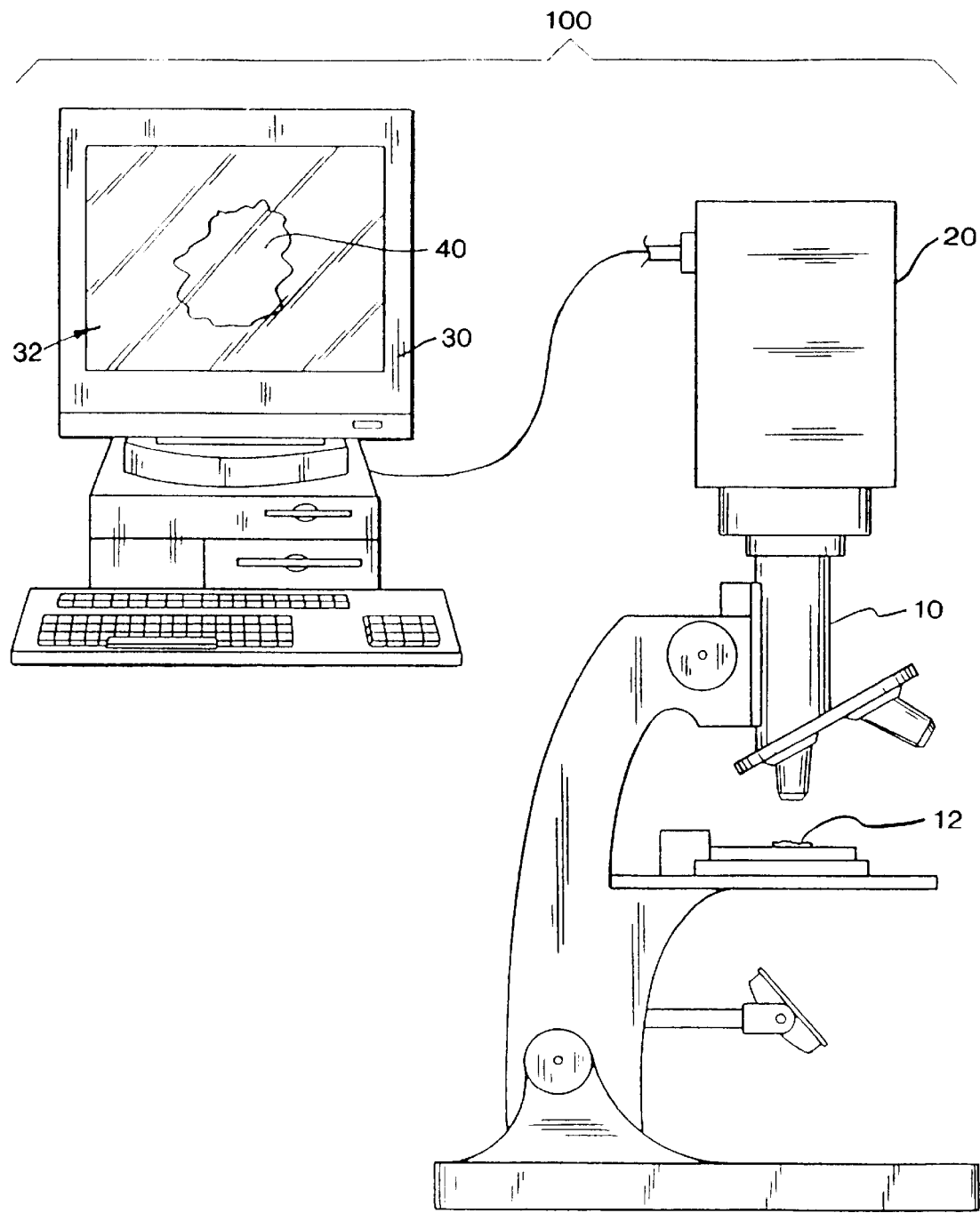
FIGS. 1 to 10 illustrate the individual steps and apparatus of digital image processing and analysis from the raw image of a cancer cell to the determination of its fractal dimension.

The present invention relates to a method for identification or classification of a biological material including parts thereof which comprises: providing a digitized image defined by pixels of a material in a memory of a computer with a range of grey level values and including small sized artifacts in and around the material; representing the range of grey level values in binary form using a minimum grey level value determined by a distribution of the grey level values of the pixels; removing the artifacts by eliminating general clusters of pixels of a minimum number; determining a perimeter surface of the material to be measured; measuring a fractal dimension of the perimeter surface of the material; and identifying or classifying the material based upon the fractal dimension.

Further, the present invention relates to a system for identifying biological materials including parts thereof which comprises: a microscope adapted to view a sample containing the material; and a digital means mounted on the microscope and connected to the computer to download a digital image of the material so that the program can perform a method which comprises providing a digitized image defined by pixels of a material in a memory of a computer with a range of grey level values and including small sized artifacts in and around the material; representing the range of grey level values in binary form using a minimum grey level value determined by a distribution of the grey level values of the pixels; removing the artifacts by eliminating general clusters of pixels of a minimum number; determining a perimeter surface of the material to be measured; measuring a fractal dimension of the perimeter surface of the material; and identifying or classifying the material based upon the fractal dimension.

Finally, the present invention relates to a method for identifying a cell which is diagnostically relevant, the improvement which comprises analyzing the fractal dimension of the cell and determining whether the cell is diagnostically relevant based upon the fractal dimension. Such a cell can be for instance a lymphocyte with hairy cell leukemia.

The term "biological material" as used herein means any living plant or animal such as a virus, bacteria, yeast, mold, protozoa, algae including procaryotes and eucaryotes and any parts of such plants or animals particularly, cells and tissues formed of multiple cells of subcellular components such as nuclei and mitochondria. The method and system of the present invention is particularly adapted for very small sized particles of the biological material having a particle size between about 0.1 and 100 microns which are generally the same in nature. The biological material can be non-living or living.

The term "grey level value" represents image intensity of each of the pixels of the image and does not necessarily refer to actual color (i.e. "grey") of the pixel or image. The images can be represented in any colors not limited to black, white and grey. In the preferred embodiment, the grey level values of the pixels range between 0 and 255.

As shown in FIG. 1, a microscope 10 is used to provide an image 40 of small sized biological materials. Such microscopes 10 can use various means of imaging including light, confocal laser, electron and atomic force imaging. Under light imaging there is laser and phase contrast and fluorescent imaging for instance. Such microscopes 10 are well known to those skilled in the art and are well described in the patent literature for instance.

Digitizing of the image 40 of the biological material is accomplished by digital microprocessor means. Preferably, a digitizing charge coupled device (ccd) camera 20 is focused through the microscope 10 or directly on the biological material to provide the data. Alternatively, a picture can be produced from the microscope 10 which can be digitized using an optical scanner and then the digitized data incorporated into the computer 30. Under some circumstances the microscope 10 can provide digitized data directly, assuming it is produced in this form in the microscope 10.

The particular purpose of this invention is to provide an accurate, quantitative, and reliable method and system for the identification and/or classification of small biological materials, such as individual cells 12 of human or non-human origin, as well as microorganisms, such as bacteria or viruses, in terms of a scalar, one-dimensional observation. To accomplish this task, the fractal dimension D of the perimeter surface of these biological materials is determined. This invention can be used to distinguish different species of bacteria or different cell types. In particular, the invention can be used to differentiate between neoplastic and healthy cells in humans via the analysis of cell sections obtained from a biopsy, cell suspensions obtained by aspiration, and the like.

It has been found that the shape and surface of biological materials or cells as with many naturally occurring systems can not be described adequately by Euclidean geometry alone. Thus, fractal (geometry) analysis was developed to describe those systems unable to be described by conventional Euclidean geometry. The power-law dependence which is used to determine the fractal dimension D of a system is based on the premise that systems having a fractal dimension D also have self-similarity. Thus, the system is invariant to changes of scales, it possesses dilational symmetry and consequently, there exists no characteristic length scale associated with the structure. A description and explanation of fractal dimensions, the power-law and self similarity is found in "Fractals in Chemistry, Geochemistry, and Biophysics" by K. S. Birdi, pages 1 to 10.

Figure 9:
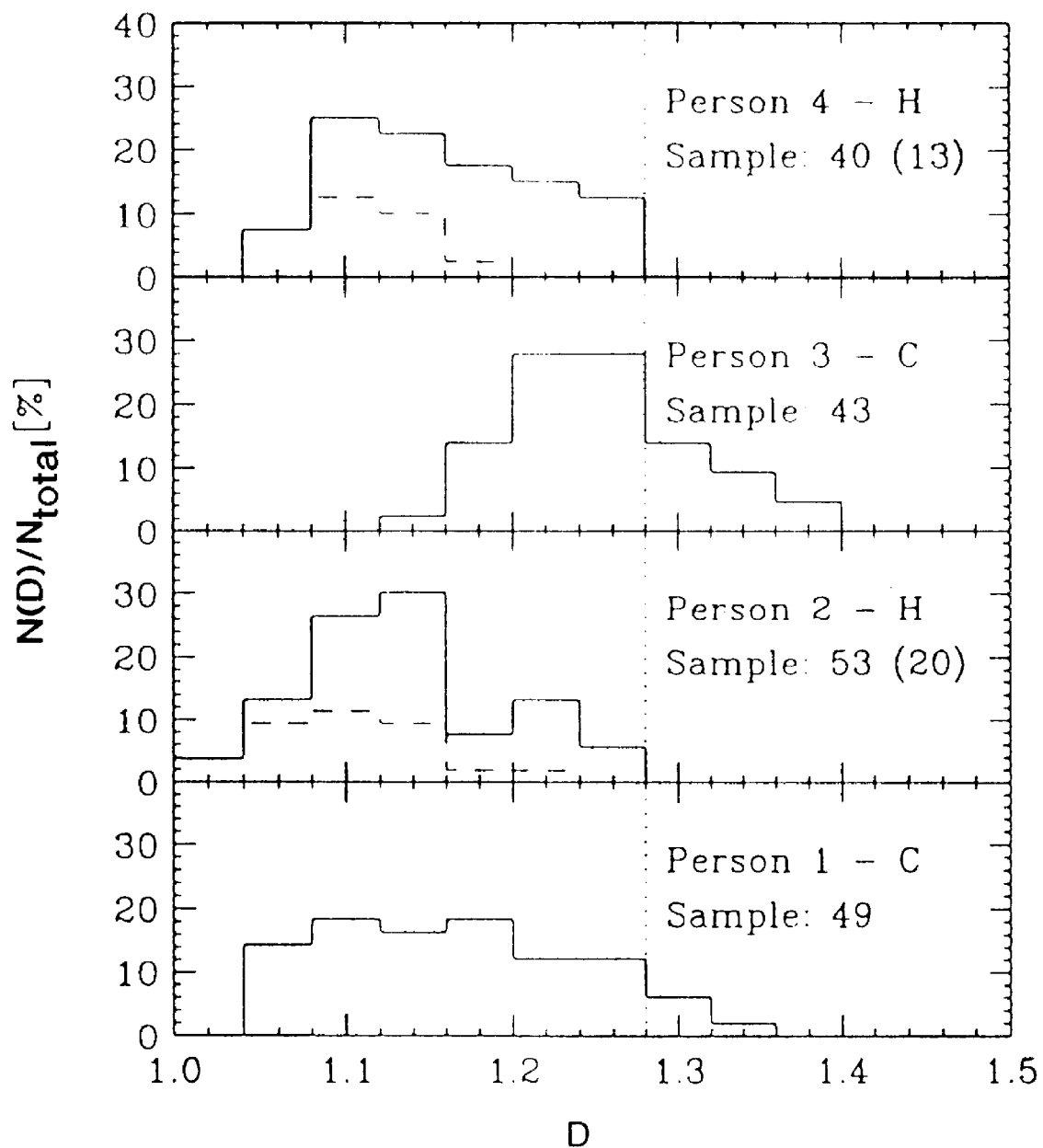

The method and system of the present invention allow for the quantitative classification of cells 12 or other small biological materials in terms of a single number, namely the fractal dimension D of the perimeter surface 40D of the cell 12. This method can be used to collect information from a large number of cells 12 and present the information in histogram form (FIG. 9). The histogram can be used to make statistical inferences regarding the classification of the sample. The most important application of this invention lies in its utility for the differentiation of neoplastic and non-neoplastic human cells 12 of a given type.

The method and system can be used in two modes. In the first mode, the method and system are used as a fully automated diagnostic tool, returning a probability of cancer including a confidence level. Since the analysis is done by a computer 30, a very large number of samples can be processed. In the second mode, the method and system can be used as a preselection device, filtering out only the individual cells 12 having the highest probability for malignancy to be visually re-examined by the pathologist. This greatly reduces the number of cells having to be visually inspected while increasing the total number of processed cells.

Figure 2:
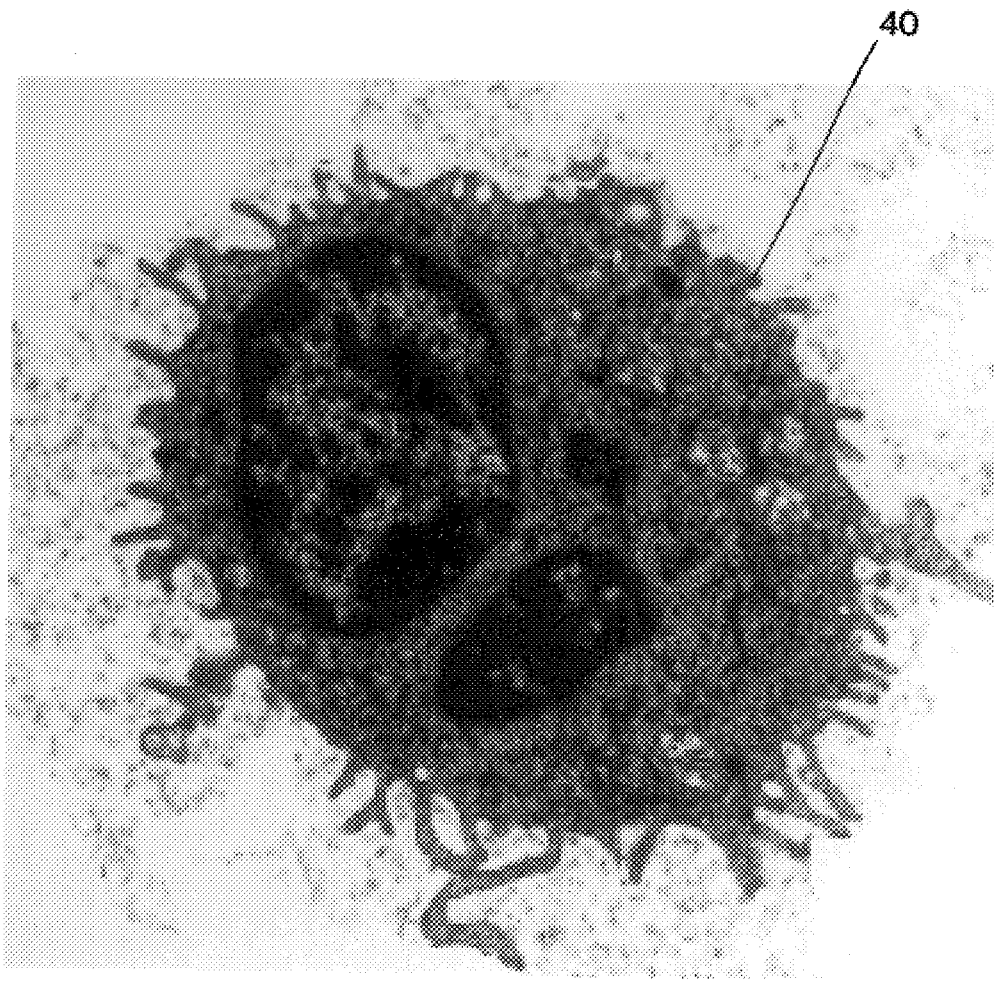

As shown in FIG. 1, a microscope 10, a camera 20 and a computer 30 with the software are used to facilitate the analysis. Samples for examination under the microscope 10 are prepared in conventional ways depending upon the type of microscope 10 used. These samples can either be complete organic structures or sections of organic structures. Pictures of the organic samples under the microscope 10 are taken with the camera 20. In the preferred embodiment, the images 40 are digitized by the camera 20 and then transferred into the computer memory. This is done by using a ccd-digitizing camera 20 with at least 1000×1000 pixels and 256 grey level values per pixel. Alternatively, regular pictures can be used which are then digitized using an optical scanner (not shown) to produce a digitized image 40 which is fed into the computer 30. Once in the computer 30, the digital image 40 (FIG. 2) is processed in five steps by the computer software to extract the fractal dimension D information. In addition, the digital images 40 are stored for possible later visual examination by the physician/pathologist.

Figure 3:
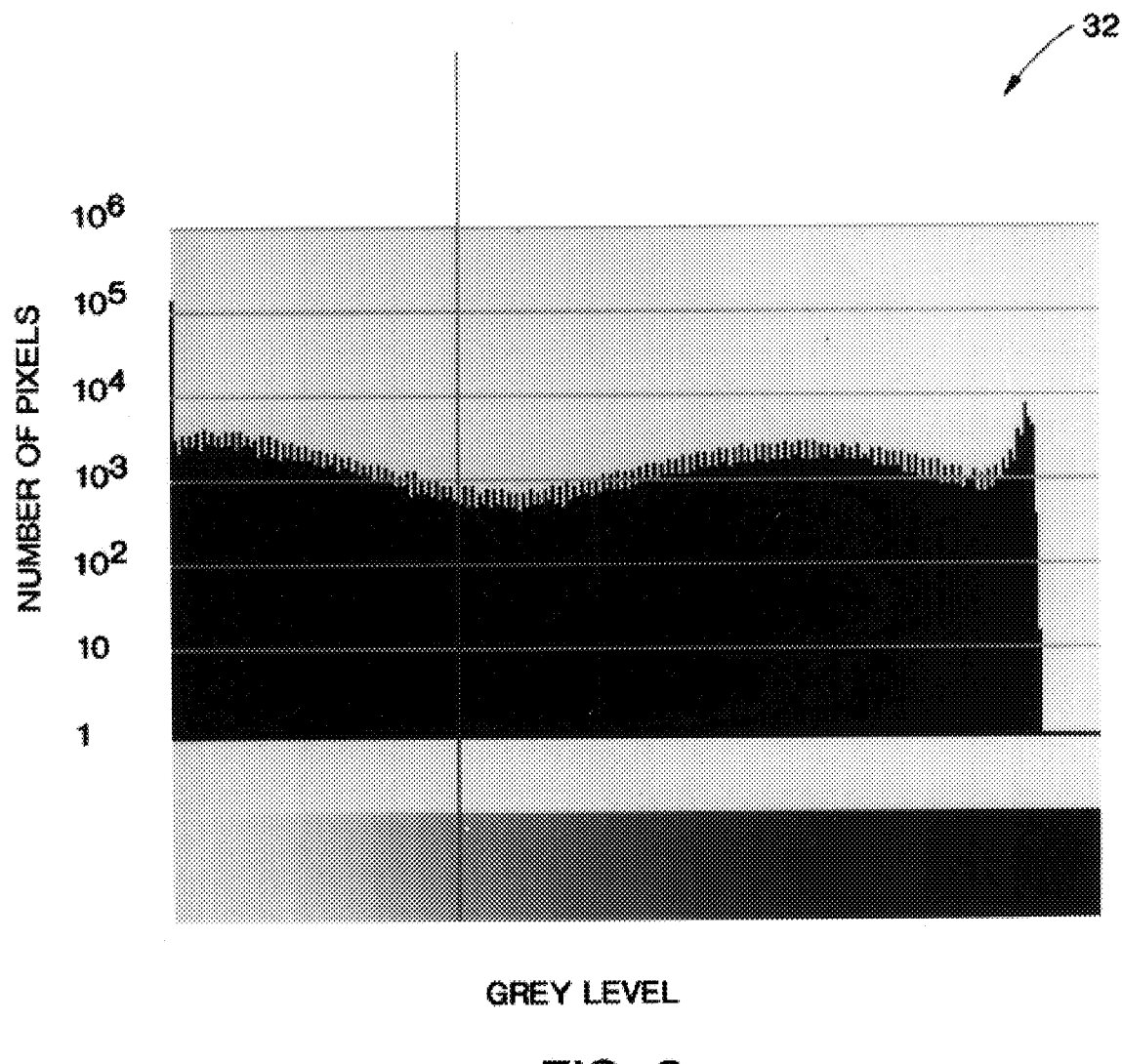
Figure 4:
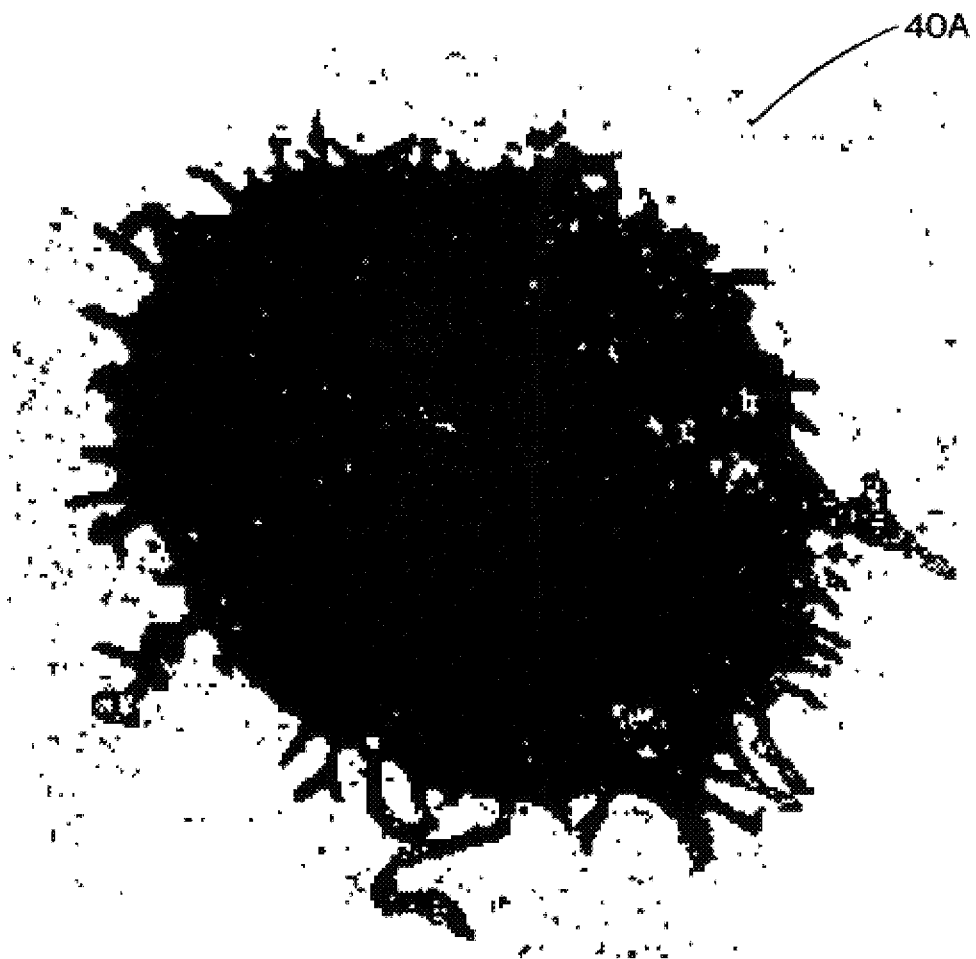
Figure 5:
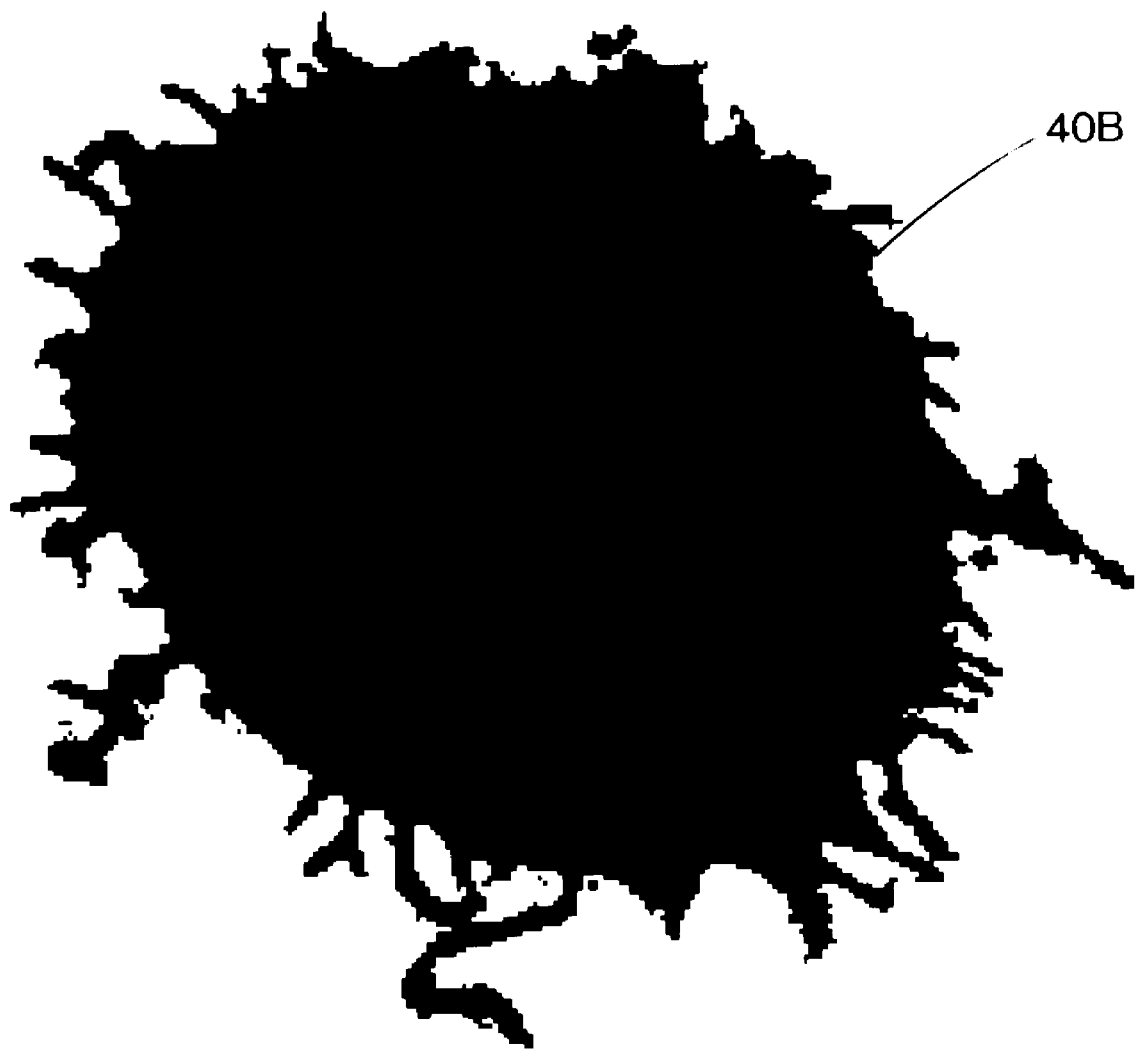
Figure 6:
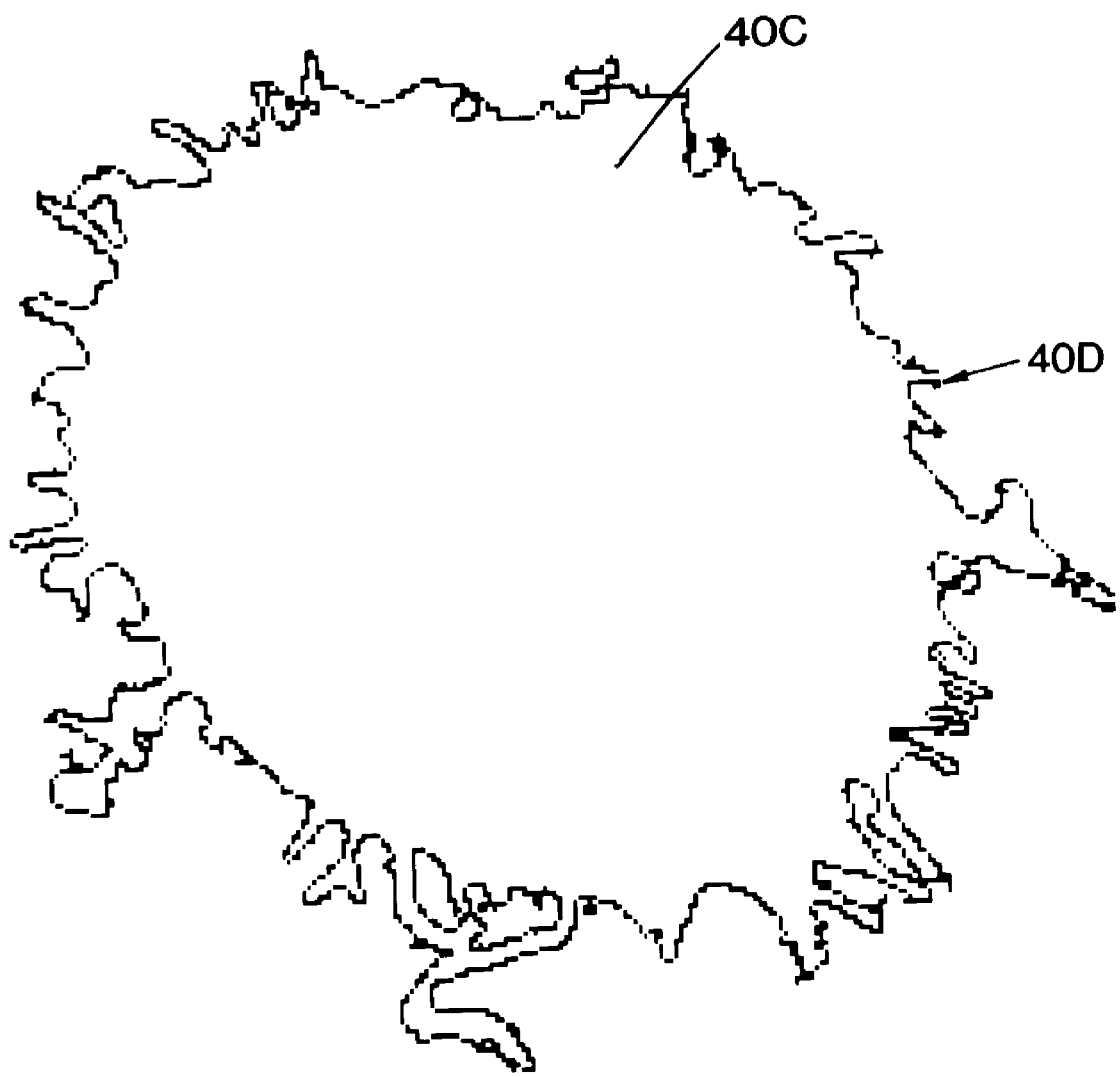

In the first step, a grey level value threshold is set. The pixels of the image 40 are then processed such that all pixels having grey level values above the preset grey level value threshold are converted into black and are assigned a predetermined binary value and all pixels having grey level values below the preset threshold are converted into white and are assigned the alternate binary value (FIG. 4). Thus, all pixels are represented by either a one (1) or a zero (0). The appropriate threshold is obtained by finding a local minimum in the grey level value distribution histogram of the individual pixels of the digital image 40 (FIG. 3). As described in U.S. Pat. No. 4,538,299, to DeForest such threshold declination is well known in the prior art. In the second step, corrections for small inclusions resulting from the digitization process are made. This step is preformed by the cluster_flip subroutine as shown in the computer program listing of Appendix I. These corrections are made using a unique cluster recognition algorithm, which finds small enclosed clusters (black in white or white in black) and flips their grey level value from white to black or vice-versa. The second step eliminates holes in the interior of the image 40A and specks on the outside of the image boundary (FIG. 5). In the third step, the boundary of the surface or perimeter surface 40D of the cell 12 is found by taking derivatives of the remaining grey level value distribution in both spatial directions (FIG. 6). The method uses the binary representation of the grey level value of the pixels of the images 40C to determine the pixels which represent the perimeter surface 40D of a cell 12. The resulting perimeter surface points are used to determine the fractal dimension D of the cell 12. In the preferred embodiment, 5,000 to 10,000 perimeter surface points are used for each cell 12. The method for determining the perimeter surface points is similar to those known in the prior art. The methods and system used to capture and digitize the image 40 of the sample are also well known in the prior art. Likewise, the method and apparatus for enhancing the digitized image 40 using grey-scaling threshold declination are well known in the prior art. However, the cluster recognition and elimination method for removing small impurities and further enhancing the image 40D are unique to Applicant's invention.

Figure 7:
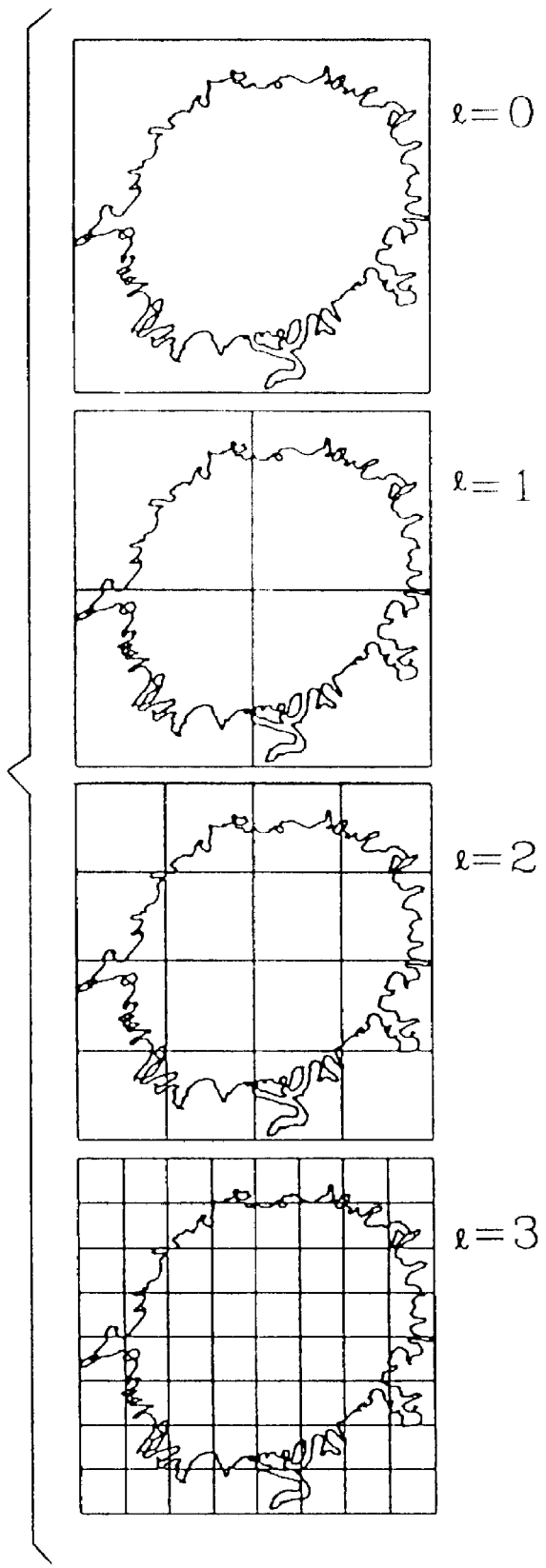

As shown in FIG. 7, a box counting method is applied to the enhanced digital cell image 40C of the cell 12 to determine the size and shape of the surface of the sample cell 12 and consequently, the fractal dimension D of the perimeter surface 40D of the sample cell 12. First, the enhanced image 40C of the cell 12 is divided into a number of boxes n with sidelength s. In the preferred embodiment, $s=2^{-l}$ where l is the resolution. Next, the number of boxes N(l) intersected by the surface of the cell 12 or occupied boxes is counted and recorded. The number of boxes N(l) intersected by the perimeter surface 40D of the cell 12 is a function of the sidelength s of the boxes or resolution l and the total number of boxes n. This process is repeated for various different resolutions l preferably two (2) through seven (7). Preferably, after each calculation, the resolution l is increased by one thus, the sidelength s of the box is reduced by half to provide the sidelength s of the boxes for the next box counting calculation. As the resolution l is increased, the sidelength s of the box decreases, which increases the number of boxes N(l) touched by the perimeter surface 40D of the cell 12 and consequently, the accuracy of the measurement increases. Thus, the ideal final box counting process would follow the following equation:

$$\text{Lim}_{n \to \infty} N(l,n) = N(l) = \text{Constant} \cdot S^{-D}$$

where $s=2^{-l}$ and D is the fractal dimension of the perimeter surface 40D of the cell 12. However, since we are working with only a finite number of pixels, there is a practical maximum value of l, $1 \leq 12$.

Figure 8:
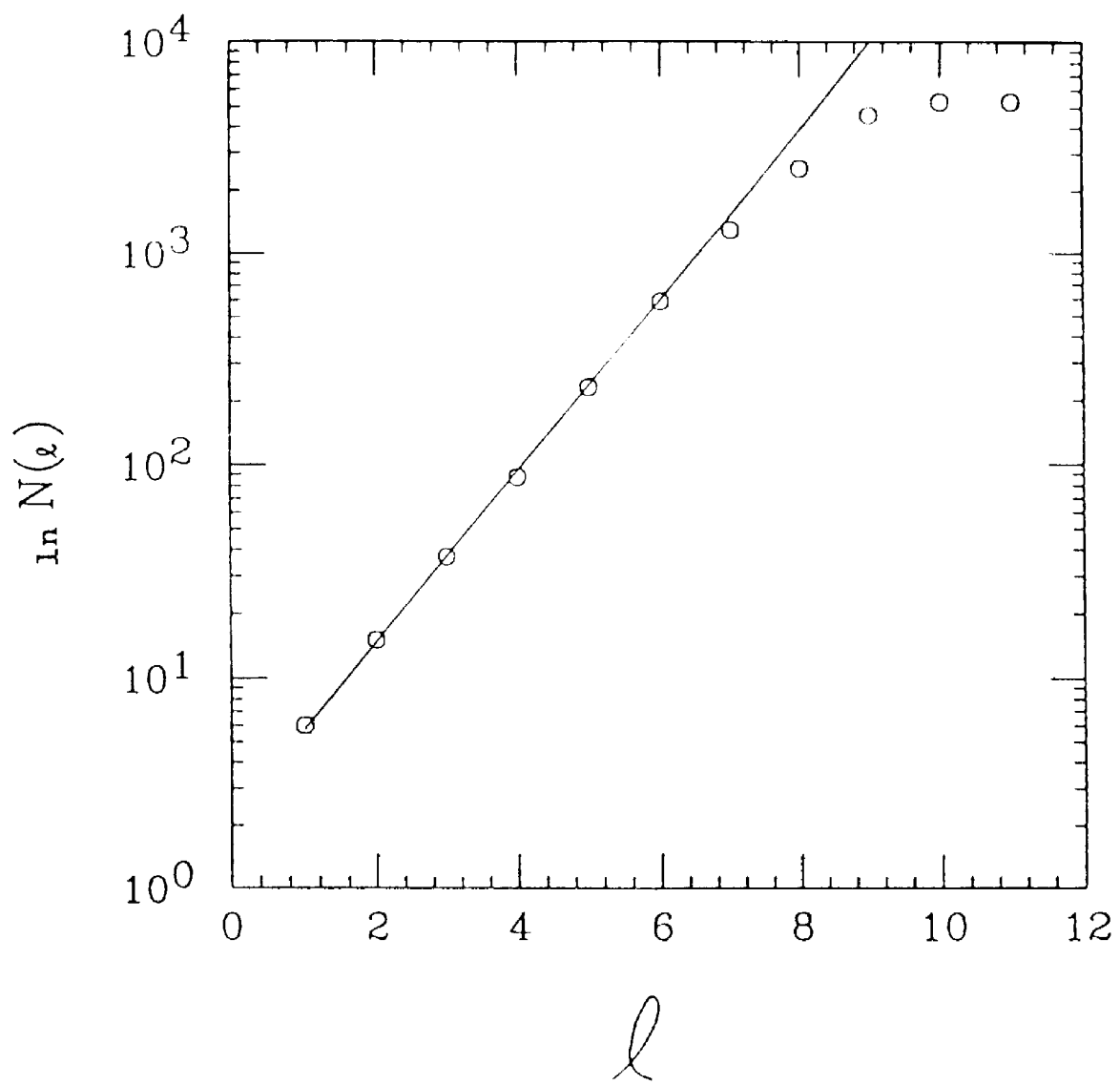

The input used in the fractal analysis subroutine in the software, as shown in Appendix I, is the perimeter surface points of the cell 12. In the preferred embodiment, the number of surface points input for each cell 12 is between 5,000 and 10,000 and preferably no greater than 1,000,000 points are used. The box counting subroutine counts the number of boxes N(l) occupied by the perimeter surface points of the cell 12 for boxes having different sidelengths s. In the preferred embodiment, the box counting subroutine Fractal_old is used for preforming fractal analysis on the perimeter surface points of the cell 12. The power-law is then applied to the resulting box totals and the natural log of the number of occupied boxes N(l) is then plotted versus the resolution l (FIG. 8). Once the number of occupied boxes N(l) for each cell 12 has been calculated and plotted, a straight line is then fit along the points using the maximum and minimum pair (FIG. 8). The straight line is a linear regression fit to the data points representing the number of occupied boxes N(l) at each resolution l. Applying standard, well-known numerical techniques, the correlation coefficient (coef) of the line can be obtained. The correlation coefficient (coef) measures how close the straight line is to the actual data points. A correlation coefficient (coef) of one (1) represents an exact fit of the straight line to the data points. In the preferred embodiment, the linear regression fit of the line to the data points typically results in a correlation coefficient (coef) of 0.99 or greater. The slope of the resulting straight line represents the fractal dimension D of the particular cell 12.

Power-law analysis shows that there is a constant fractal dimension D which can be used to calculate the increase in the perimeter surface 40D of the cell 12 as the sidelength s of the boxes decreases. The surface morphometry of all biological cells 12 can be represented by a fractal dimension D. The larger the fractal dimension D of the cell 12, the greater the meandering of the surface of the cell 12. Thus, neoplastic hairy cell leukemia cells due to their uneven surface would have a higher fractal dimension D than normal blood lymphocyte cells.

As shown in FIG. 9, the resulting fractal dimension D for each cell 12 in a sample can be plotted as a histogram showing the number of cells 12 in the sample having each fractal dimension D as a percentage of the total number of cells 12 in the sample. The particular histogram for an unknown sample is then compared with a similar histogram calculated using the same method and system of a known sample. By comparing the histogram of the unknown sample with the histogram of the known sample, the classification of the unknown sample can be quantitatively determined with a calculated degree of certainty. In the preferred embodiment, the cells 12 which are indicated to be of interest or abnormal are further examined visually by a pathologist who determines whether or not the unknown sample is from a healthy person or a person with hairy-celled leukemia.

The method and system increases the total number of cells 12 analyzed while reducing the actual number of cells 12 visually examined by the pathologist. Due to the use of the computer 30, a large number of individual cells 12 can be analyzed quickly and accurately enabling the pathologist to obtain the same accurate results by visually examining less cells 12. Furthermore, by collecting and binning the information on the individual effective fractal dimensions D, a histogram can be obtained. This histogram enables the distinction between neoplastic and non-neoplastic cell samples to be made, if necessary, without the need for further examination by the pathologist.

Figure 10:
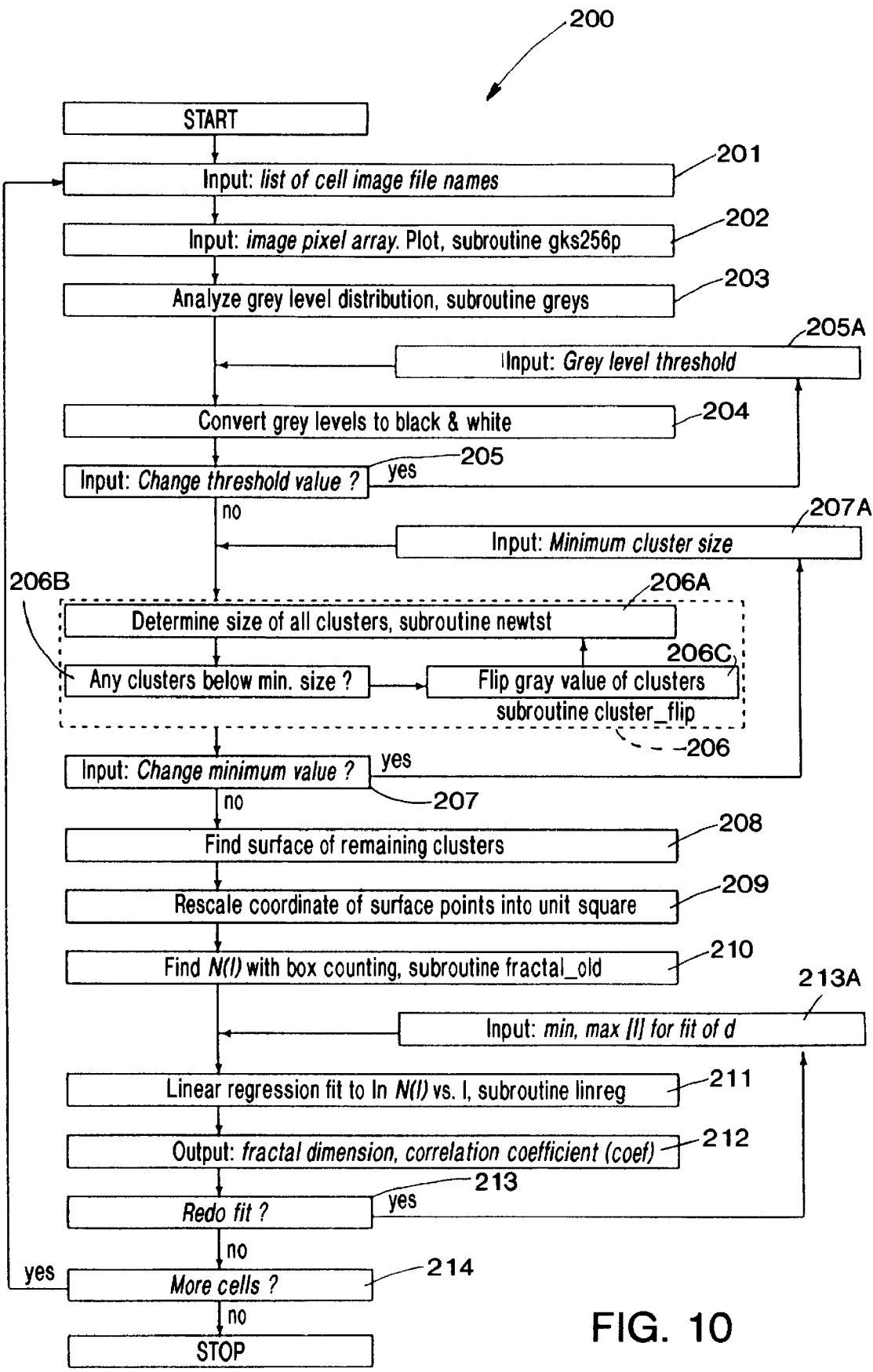

The steps of the method preformed by the computer software are set forth in the flow chart 200 of FIG. 10. In the first step 201, the user inputs the list of file names containing the digital data representing the initial unenhanced image 40 (FIG. 2) of the cell 12 into the computer 30. Next, the grey level values for each pixel are read from the input file step 202, and the grey level distribution of the grey level values is plotted, step 203 (FIG. 3). The grey level value threshold is obtained by finding a local minimum in the grey level value distribution histogram (FIG. 3) of the individual pixels, step 203. Using the grey level value threshold as the dividing mark, the grey level values of the pixels are converting to either black or white depending upon whether the grey level value of the pixel is above or below the grey level threshold, step 204. The result is printed as FIG. 4. Once all the pixels have been converted to black or white, the user is asked whether or not they wish to input a new grey level value threshold, step 205. If a new threshold is entered, step 205A then the program repeats steps 204 and 205. The above loop will continue as long as the user continues to enter a new grey level value threshold, step 205A. The user may select a new threshold if for some reason the grey level threshold calculated by the computer program did not produce an adequate representation of the cell image 40A. The program then enters the cluster_flip subroutine, step 206 where the size of cluster is determined, step 206A and those clusters smaller than a given size are flipped, steps 206B and 206C. A cluster is a group of pixels of all one color either black or white. Those pixels of a cluster smaller than a set cluster size are flipped by having their color changed from white to black or black to white. Thus, the small clusters become the same color as the surrounding pixels. This subroutine eliminates impurities or imperfections inside and outside the cell image 40A thus, providing enhanced image 40B (FIG. 5). Once all the clusters smaller than the minimum cluster size are flipped, the program exits the cluster_flip subroutine. At this point, the user is asked whether or not they wish to enter a new minimum cluster value, step 207. If the user enters a new minimum cluster size, step 207A, the program will re-enter the cluster_flip subroutine 206 and re-examine the clusters eliminating those smaller than the new minimum cluster size. The user may choose to use a new minimum cluster size if the original cluster size chosen by the computer does not adequately eliminate the necessary clusters or if essential clusters are eliminated. The user can keep adjusting the minimum cluster size until the image 40B is enhanced to his satisfaction. Next, the surface points of the remaining clusters are found and plotted, step 208. The remaining clusters should represent cells 12 and the surface points should accurately depict the perimeter of the cell 12 (FIG. 6). In step 209, the coordinates of the surface points are rescaled into one (1) square unit (FIG. 6, l=0). The program then uses a fractal box counting algorithm in the fractal_old subroutine to determine the fractal dimension of the cell, step 210. The box counting method finds N(l), the number of boxes touched by the surface points of a cell 12 of the image 40C, at a given resolution l preferably, l=(2–7). The natural logarithm, lnN(l), of the results is then plotted versus l, step 211 (FIG. 8). Finally, in the linreg subroutine a liner regression fit to the plot lnN(l) versus l is preformed to obtain a straight line, step 211. From this plot, the fractal dimension D for the cell is obtained, step 212. In addition, the correlation coefficient relating to the fit of the line to the data points is obtained from the plot, step 212. If the correlation coefficient is not close to one, the user is given the opportunity to redo the linear regression fit, step 213 and is asked to input the minimum and maximum l, step 213A. This is necessary since all points of l are used to produce the straight line as shown in FIG. 8. Usually l is 3 to 7. The entire process can then be repeated for additional cells as necessary, step 214.

All of the algorithms and subroutines necessary for the image processing and the determination of the fractal dimension D and the plotting of the results are in Appendix I.

EXAMPLE 1

Healthy human white blood cells and neoplastic blood cells (hairy-cell leukemic lymphocytes), were differentiated by the method and system. The results for known hairy cell leukemia cases and for control samples taken from healthy persons show that the fractal dimension histogram achieved through use of this method and system is well able to be used to distinguish between the two types of cells 12. As shown in FIG. 9, none of the cells 12 from the healthy persons had a fractal dimension D greater than 1.28 (Persons 2 and 4). Thus, cells 12 having a fractal dimension D greater than 1.28 were considered unhealthy leukemic cells and thus it was determined that persons (Persons 1 and 3) who had cells 12 with fractal dimension D greater than 1.28 had hairy cell leukemia. This result was confirmed by independent methods.

The present invention can be used with neoplastic cells and microorganisms such as bacteria, virus, amoeba, fungi and including procaryotic and eucaryotic cells. All such variations are well known to those skilled in the art.

It is intended that the foregoing description be only illustrative of the present invention and that the present invention be limited only by the hereinafter appended claims.

APPENDIX I

-21-

```
      program analyze_many_pict
*
* Fractal dimension analysis of perimeter of cell section for cancer
* recognition.  Image processing included.
*
* Author:  Wolfgang Bauer, 1993, 1994
* Remark:  This version uses GKS software plotting on the screen
*
      implicit    none
      integer     nmax, imax
      parameter   (nmax=1000,imax=100000)
      byte        pixel(512)
      character*80 infile,answer
      integer*2   array(nmax,nmax), array1(nmax,nmax)
      integer     p(256,256)
      integer     c1, c2, c3, ws1, ws2, ws3
      integer     nx, ny, i, j, k, num, nflip, maxsize, iopt, ipass,
     &            ngrey, levels, n, npt, npass, nch, n_input, ipt,
     &            l, lmin, lmax, ifile, nfile, nxs, nys, nstep, inunit,
     &            nfmin, iii, long
      real        Nocc(10), x(100), y(100), dim, coef, A, B
      real        r(2,imax)
      print *, ' Number of input files (min and max)?'
      read  *, nfmin,nfile
      print *, ' Long output desired? Yes: 1, else no'
      read  *, long
      print *, ' input file name for file list (blank -> terminal)'
      read (*,'(a)') infile
      if (infile(1:1) .eq. ' ') then
        inunit = 6
      else
        inunit = 55
        open(unit=55,file=infile,status='old')
      end if
      print *, ' output file name for results '
      read (*,'(a)') infile
      open(unit=60,file=infile,status='new')
      call gopks(1,0)              ! open GKS
      call gopwk(1,c1,ws1)         ! open workstation using defaults
      call gks256(p,1,c1,ws1)      ! draw an empty window
      call gopks(2,0)              ! open GKS
      call gopwk(2,c2,ws2)         ! open workstation using defaults
      call gks256(p,2,c2,ws2)      ! draw an empty window
      call gopks(3,0)              ! open GKS
      call gopwk(3,c3,ws3)         ! open workstation using defaults
      call gks256(p,3,c3,ws3)      ! draw an empty window
      call gdawk(1)                ! deactivate workstation
      call gdawk(2)                ! deactivate workstation
      call gdawk(3)                ! deactivate workstation
      write(60,'(a)')
     & '     Nx    Ny    Npt D-fractal Cor.Coeff N(1) N(2) N(3) N(4) N(5)
     &N(6) N(7) N(8) N(9) N(10) lmin lmax nfli maxs Input file name'
      do ifile = 1,nfile
        if (inunit .eq. 55) then
          read (55,'(a)') infile
          write(*,'(i4,'': Current data file: '',a40)') ifile,
     &          infile(1:40)
        else
          print *, ' enter new input file name', ifile
          read (*,'(a)') infile
```

```
            end if
            if (ifile .lt. nfmin) goto 65
            open(unit=50,file=infile,status='old',form='unformatted')
            read(infile,'(1x,i3,1x,i3)') nx, ny
            if (nx .gt. nmax .or. ny .gt. nmax) then
              print *, ' *** Fatal Error - Program Terminated ***'
              print *, ' Nx and Ny must be smaller than', nmax+1
              stop     '*****************************************'
            end if
            do j = 1,nmax
              do i = 1,nmax
                array(i,j) = 0
                array1(i,j) = 0
              end do
            end do
            j = 1
            i = 1
5           continue
            read(50,end=10) pixel
              do k = 1,512
                num = pixel(k)
                if (num .lt. 0) num = num + 256
                num = 255 - num
                array(i,j) = num
                i = i + 1
                if (i .gt. nx) then
                  i = 1
                  j = j + 1
                  if (j .gt. ny) goto 10
                end if
              end do
            goto 5
10          close(50)
            do j = 1,ny
              do i = 1,nx
                array1(nx+1-i,j) = array(i,j)
              end do
            end do
            do j = 1,ny
              do i = 1,nx
                array(i,j) = array1(i,j)
              end do
            end do
            if (nx .le. 256 .and. ny .le. 256) then
              nstep = 1
            else if (nx .le. 512 .and. ny .le. 512) then
              nstep = 2
            else if (nx .le. 768 .and. ny .le. 768) then
              nstep = 3
            else
              nstep = 4
            end if
            do j = 1,256
              do i = 1,256
                p(i,j) = 0
              end do
            end do
            do j = 1,ny,nstep
              do i = 1,nx,nstep
                p(1+(i-1)/nstep,1+(j-1)/nstep) = array(i,j) / 4
              end do
```

-23-

```
        end do
        call gacwk(1) ! activate workstation
        call gks256p(p,1)
        call gdawk(1) ! deactivate workstation
        if (long .eq. 1) then
          iii = 20
          write(iii) p
          iii = iii+1
        end if
        call greys(nx,ny,array,p)
        call gacwk(3) ! activate workstation
        call gks256p(p,3)
        call gdawk(3) ! deactivate workstation
20      print *, ' Threshold greylevel ? (-1 => accept current value)'
        read *, n_input
        if (n_input .eq. -1) goto 25
        nflip = n_input
        do j = 1,ny
          do i = 1,nx
            if (array(i,j) .le. nflip) then
              array1(i,j) = 0
            else
              array1(i,j) = 255
            end if
          end do
        end do
        do j = 1,256
          do i = 1,256
            p(i,j) = 0
          end do
        end do
        do j = 1,ny,nstep
          do i = 1,nx,nstep
            p(1+(i-1)/nstep,1+(j-1)/nstep) = array1(i,j) / 4
          end do
        end do
        call gacwk(2) ! activate workstation
        call gks256p(p,2)
        call gdawk(2) ! deactivate workstation
        if (long .eq. 1) then
          write(iii) p
          iii = iii+1
        end if
        call greys(nx,ny,array,p)
        do i = 1,256
          p(nflip,i) = 30
        end do
        call gacwk(3) ! activate workstation
        call gks256p(p,3)
        call gdawk(3) ! deactivate workstation
        if (long .eq. 1) then
          write(iii) p
          iii = iii+1
        end if
        goto 20
25      continue
        do j = 1,ny
          do i = 1,nx
            array(i,j) = array1(i,j)
          end do
        end do
```

-24-

```
        ipass = 0
        do j = 1,256
          do i = 1,256
            p(i,j) = 0
          end do
        end do
28      print *, ' Maximum cluster flip size? (-1 => keep value)'
        read *, n_input
        if (n_input .eq. -1) goto 35
        maxsize = n_input
        do j = 1,ny
          do i = 1,nx
            array1(i,j) = array(i,j)
          end do
        end do
        npass = 0
30      call cluster_flip(array1,nx,ny,maxsize,nch)
        npass = npass + 1
        if (nch .gt. 0 .and. npass .lt. 20) goto 30
        do j = 1,ny,nstep
          do i = 1,nx,nstep
            p(1+(i-1)/nstep,1+(j-1)/nstep) = array1(i,j) / 4
          end do
        end do
        if (ipass .eq. 1) then
          call gks256p(p,3)
          if (long .eq. 1) then
            write(iii) p
            iii = iii+1
          end if
        else
          ipass = 1
          call gacwk(3)   ! activate workstation
          call gks256p(p,3)
          if (long .eq. 1) then
            write(iii) p
            iii = iii+1
          end if
        end if
        goto 28
35      continue
        call gdawk(3)   ! deactivate workstation
        do j = 1,ny
          do i = 1,nx
            array(i,j) = array1(i,j)
          end do
        end do
        npt = 0
        do j = 2,ny-1
          do i = 2,nx-1
            if (array(i,j) .eq. 255) then
              if (array(i+1,j  ) .eq. 0 .or.
     &            array(i-1,j  ) .eq. 0 .or.
     &            array(i  ,j-1) .eq. 0 .or.
     &            array(i  ,j+1) .eq. 0) then
                npt = npt + 1
                r(1,npt) = float(i)
                r(2,npt) = float(j)
              end if
            end if
          end do
```

-25-

```
      end do
      if (npt .eq. 0) then
        print *, ' Present cell skipped - no surface points found'
        goto 65
      end if
      do j = 1,256
        do i = 1,256
          p(i,j) = 0
        end do
      end do
      do ipt = 1,npt
        i = 1+nint(r(1,ipt)-1.)/nstep
        j = 1+nint(r(2,ipt)-1.)/nstep
        p(i,j) = 63
      end do
      call gacwk(2) ! activate workstation
      call gks256p(p,2)
      call gdawk(2) ! deactivate workstation
      if (long .eq. 1) then
        write(iii) p
        iii = iii+1
      end if
      call FRACTAL_old(r,npt,Nocc)
45    continue
      do j = 1,256
        do i = 1,256
          p(i,j) = 0
        end do
      end do
      do i = 1,256
        p(6,i) = 20
        p(i,6) = 20
      end do
      do l = 1,10
        i = l*24 + 6
        j = nint(20.*log(Nocc(l))) + 6
        if (j .le. 254) then
          p(i,j) = 63
          p(i+1,j) = 63
          p(i+2,j) = 63
          p(i-1,j) = 63
          p(i-2,j) = 63
          p(i,j+1) = 63
          p(i,j+2) = 63
          p(i,j-1) = 63
          p(i,j-2) = 63
        end if
      end do
      call gacwk(3) ! activate workstation
      call gks256p(p,3)
      if (long .eq. 1) then
        write(iii) p
        iii = iii+1
      end if
      print *, ' Minimum and maximum l-value for dimension fit'
      read *, lmin, lmax
      do l = 1,10
        if (l .ge. lmin) then
          x(l-lmin+1) = l
          y(l-lmin+1) = log(Nocc(l))
        end if
```

-26-
```
      end do
      call linreg(x,y,lmax-lmin+1,dim,coef,A,B)
      do i = 30,200
         j = nint(20.*(A+B*real(i-6)/24.)) + 6
         if (j .gt. 0 .and. j .lt. 257) p(i,j) = 40
      end do
      call gks256p(p,3)
      call gdawk(3) ! deactivate workstation
      if (long .eq. 1) then
        write(iii) p
        iii = iii+1
      end if
      write(*,'(2i5,i7,2f10.5,7i6)')
     &        nx,ny,npt,dim,coef,(nint(Nocc(l)),l=1,7)
      print *, ' Enter: 1 - to redo fit'
      print *, '        2 - to skip present cell'
      print *, '        3 - to quit after this cell'
      read(*,'(a)') answer
      if (answer(1:1) .eq. '1') goto 45
      if (answer(1:1) .eq. '2') goto 65
      write(60,'(2i5,i7,2f10.5,i4,5i5,4i6,4i5,1x,a20)')
     &        nx,ny,npt,dim,coef,(nint(Nocc(l)),l=1,10),
     &        lmin, lmax, nflip, maxsize, infile(1:20)
      if (answer(1:1) .eq. '3') goto 75
 65   continue
      end do
 75   continue
      stop ' ------------------ D O N E ------------------'
      end subroutine cluster_flip(array,nx,ny,maxsize,mchange)
      parameter (nmax=1000)
      parameter (maxx=nmax,maxy=nmax)
      integer*2 array(maxx,maxy)
      LOGICAL*1 CLSTMB(maxx,maxy)
      INTEGER   NEWPTS(maxx*maxy,2)
      COMMON    CLSTMB, NEWPTS
      multip = 0
      mchange = 0
      do iy = 1,ny
        do ix = 1,nx
          clstmb(ix,iy) = .false.
        end do
      end do
      DO IY = 1,NY
        DO IX = 1,NX
          IF(.NOT.CLSTMB(IX,IY)) THEN
            CLSTMB(IX,IY) = .TRUE.
            NEWPTS(1,1) = IX
            NEWPTS(1,2) = IY
            IMINO = 1
            IMAXO = 1
1400        CONTINUE
              IMIN = IMAXO + 1
              IMAX = IMIN
              DO 1500 I = IMINO,IMAXO
                IIX = NEWPTS(I,1)
                IIY = NEWPTS(I,2)
                if(iix.gt.    1)
     &             CALL NEWTST(IIX-1,IIY  ,IIX,IIY,IMAX,array)
                if(iix.lt.maxx)
```

-27-

```fortran
     &              CALL NEWTST( IX+1,IIY  ,IIX,IIY,IMAX,array)
                if(iiy.gt.   1)
     &              CALL NEWTST(IIX   ,IIY-1,IIX,IIY,IMAX,array)
                if(iiy.lt.maxy)
     &              CALL NEWTST(IIX   ,IIY+1,IIX,IIY,IMAX,array)
1500          CONTINUE
              IF(IMAX .NE. IMIN) THEN
                IMINO = IMIN
                IMAXO = IMAX - 1
                GOTO 1400
              ENDIF
              MULTIP = MULTIP + 1
              if (IMAXO .le. maxsize) then
                do ipt = 1,IMAXO
                  lx = NEWPTS(ipt,1)
                  ly = NEWPTS(ipt,2)
                  array(lx,ly) = 255 - array(lx,ly)
                end do
                mchange = mchange + 1
              end if
            END IF
        end do
      end do
      return
      END SUBROUTINE NEWTST(IPX,IPY,ICX,ICY,IMAX,array)
      parameter       (nmax=1000)
      parameter       (maxx=nmax,maxy=nmax)
      LOGICAL*1       CLSTMB(maxx,maxy)
      integer*2       array(maxx,maxy)
      INTEGER         NEWPTS(maxx*maxy,2)
      COMMON          CLSTMB, NEWPTS
      IF (CLSTMB(IPX,IPY)) RETURN
      IF (array(ICX,ICY)+array(IPX,IPY) .eq. 255) RETURN
      NEWPTS(IMAX,1)    = IPX
      NEWPTS(IMAX,2)    = IPY
      IMAX              = IMAX + 1
      CLSTMB(IPX,IPY) = .TRUE.
      RETURN
      END subroutine FRACTAL_old(r,npt,Nocc)
      IMPLICIT      NONE
      integer       npt, imax, j, l, ix, iy, i
      parameter     (imax=100000)
      real          r(2,imax), x, y, xmin, xmax, ymin, ymax, delta,
     &              occup, Nocc(10)
      integer       N(0:1024,0:1024)
      if (npt .gt. imax) stop ' *** Error: Too many surface points ***'
      xmin = r(1,1)
      xmax = r(1,1)
      ymin = r(2,1)
      ymax = r(2,1)
      do j = 2,npt
        x = r(1,j)
        y = r(2,j)
        if (x .lt. xmin) xmin = x
        if (x .gt. xmax) xmax = x
        if (y .lt. ymin) ymin = y
        if (y .gt. ymax) ymax = y
```

-28-
```
      end do
      r(1,1) = 0.999999999 * (r(1,1) - xmin) / (xmax-xmin)
      r(2,1) = 0.999999999 * (r(2,1) - ymin) / (ymax-ymin)
      do j = 2,npt
        r(1,j) = 0.999999999 * (r(1,j) - xmin) / (xmax-xmin)
        r(2,j) = 0.999999999 * (r(2,j) - ymin) / (ymax-ymin)
      end do
      do l = 1,10
        delta = 2.**(-l)
        do iy = 0,2**l
          do ix = 0,2**l
            N(ix,iy) = 0
          end do
        end do
        do i = 1, npt
          ix = int(r(1,i)/delta)
          iy = int(r(2,i)/delta)
          N(ix,iy) = N(ix,iy) + 1
        end do
        occup = 0.
        do iy = 0,2**l
          do ix = 0,2**l
            if (N(ix,iy) .gt. 0) occup = occup + 1.
          end do
        end do
        Nocc(l) = occup
      end do
      return
      END SUBROUTINE LINREG(x,y,n,dim,r,A,B)
      IMPLICIT  NONE
      INTEGER   N, I
      REAL      X(100), Y(100), X2, Y2, XY, SUMX, SUMY, SXX, SYY, SXY,
     &          R, B, A, XMEAN, YMEAN, dim
      X2   = 0.0
      Y2   = 0.0
      XY   = 0.0
      SUMX = 0.0
      SUMY = 0.0
      DO I = 1,N
        SUMX = SUMX + X(I)
        SUMY = SUMY + Y(I)
        X2   = X2 + X(I)**2
        Y2   = Y2 + Y(I)**2
        XY   = XY + X(I) * Y(I)
      END DO
      SXX   = X2 - SUMX**2 / FLOAT(N)
      SYY   = Y2 - SUMY**2 / FLOAT(N)
      SXY   = XY - SUMX * SUMY / FLOAT(N)
      R     = SXY / SQRT( SXX * SYY )
      B     = SXY / SXX
      XMEAN = SUMX / FLOAT(N)
      YMEAN = SUMY / FLOAT(N)
      A     = YMEAN - B * XMEAN
      dim = B/LOG(2.)
      RETURN
      END subroutine gks256(Spec,wsid,conid,wstype)
      implicit none
```

-29-

```
      integer wsid,Spec(256,256)    NumberOfColors,NumberMinus1,i,j,
      integer conid,wstype,num_colors,color_flag,num_indexes
      integer ErrorStatus,DCunits,RasterXmax,RasterYmax
      real r,g,b,DCxmax,DCymax,c_array(63)
      data c_array/1.,0.9841270,
     &  0.9682540, 0.9523810, 0.9365079, 0.9206349, 0.9047619,
     &  0.8888889, 0.8730159, 0.8571429, 0.8412699, 0.8253968,
     &  0.8095238, 0.7936508, 0.7777778, 0.7619048, 0.7460318,
     &  0.7301587, 0.7142857, 0.6984127, 0.6825397, 0.6666667,
     &  0.6507937, 0.6349207, 0.6190476, 0.6031746, 0.5873016,
     &  0.5714286, 0.5555556, 0.5396826, 0.5238096, 0.5079365,
     &  0.4920635, 0.4761904, 0.4603174, 0.4444444, 0.4285714,
     &  0.4126984, 0.3968254, 0.3809524, 0.3650793, 0.3492063,
     &  0.3333333, 0.3174603, 0.3015873, 0.2857143, 0.2698413,
     &  0.2539682, 0.2380952, 0.2222222, 0.2063492, 0.1904762,
     &  0.1746032, 0.1587301, 0.1428571, 0.1269841, 0.1111111,
     &  9.5238090E-02, 7.9365075E-02, 6.3492060E-02, 4.7619045E-02,
     &  3.1746030E-02, 1.5873015E-02/
      call gacwk(wsid) ! activate workstation
      call gcrsg(wsid) ! create segment
      call gqcf(wstype,ErrorStatus,num_colors,color_flag,
     &          num_indexes) ! inquire color facilities
      if(ErrorStatus.ne.0)type *,'gqcf, Error=',ErrorStatus
      do i=1,63
        r = c_array(i)
        g = r
        b = r
        call gscr(wsid,i,r,g,b)
      enddo
      call gqdsp(wstype,ErrorStatus,DCunits,DCxmax,DCymax,RasterXmax,
     &           RasterYmax) ! get display space size
      if(ErrorStatus.ne.0)then
           type *,'gqdsp, Error=',ErrorStatus
           return
      endif
      if (wsid .eq. 1) then
        call gswkvp(wsid,0.0,0.42*DCymax,0.55*DCymax,DCymax)
      else if (wsid .eq. 2) then
        call gswkvp(wsid,0.45*DCymax,0.87*DCymax,0.55*DCymax,DCymax)
      else if (wsid .eq. 3) then
        call gswkvp(wsid,0.90*DCymax,1.32*DCymax,0.55*DCymax,DCymax)
      else if (wsid .eq. 4) then
        call gswkvp(wsid,0.0,0.42*DCymax,0.0,0.45*DCymax)
      else
        stop ' Error: This value for wsid not supported'
      end if
      goto 100
      entry gks256p(Spec,wsid)
      call gcrsg(wsid) ! create segment
 100  continue
      call gca(0.,0.,1.,1.,256,256,1,1,256,256,Spec)
      call gclsg(wsid) !close seg
      call guwk(wsid,1) !update
      return
      end subroutine greys(nx,ny,array,p)
      implicit    none
      integer     nmax, i, j, k, lmax, ny, nx
      parameter   (nmax=1000)
      integer*2   array(nmax,nmax)
```

```
      integer    levels(0:255), p(256,256)
      do i = 0,255
        levels(i) = 0
      end do
      do j = 1,ny
        do i = 1,nx
          k = array(i,j)
          levels(k) = levels(k) + 1
        end do
      end do
      lmax = 0
      do i = 0,255
        if (levels(i) .gt. lmax) lmax = levels(i)
      end do
      do i = 0,255
        if (levels(i) .gt. 0) then
          levels(i) = 1 + nint(10.*log( real(levels(i)) ))
          if (levels(i) .gt. 200) levels(i) = 200
        end if
      end do
      do j = 1,256
        do i = 1,30
          p(j,i) = (j-1)/4
        end do
        do i = 31,50
          p(j,i) = 0
        end do
        do i = 51,levels(j-1)+51
          p(j,i) = 63
        end do
        do i = levels(j-1)+52,256
          p(j,i) = 0
        end do
        p(j,75) = 20
        p(j,98) = 20
        p(j,121) = 20
        p(j,144) = 20
        p(j,167) = 20
        p(j,190) = 20
      end do
      return
      end
```

We claim:

1. A method for identification or classification of a biological material having a particle size between about 0.1 and 100 microns including parts thereof which comprises:

(a) providing a microscopically enlarged digitized image defined by pixels of a material in a memory of a computer with a range of grey level values and including small sized artifacts in and around the material;

(b) representing the range of grey level values in binary form using a minimum grey level value determined by a distribution of the grey level values of the pixels;

(c) removing the artifacts by eliminating general clusters of pixels of a minimum number;

(d) determining a perimeter surface of the material to be measured;

(e) measuring a fractal dimension of the perimeter surface of the material by plotting log N(l) versus l, where N(l) is a number of boxes intersected by a surface of the material and l is a resolution representing a number of the boxes and wherein fractal dimension is a straight line slope of the plot where l is at least between 3 and 7; and (f) identifying or classifying the material based upon the fractal dimension.

2. The method of claim 1 wherein in step (a) the digital image is derived by digitizing a view of the material.

3. The method of claim 2 wherein in step (a) the digital image is derived by means of a digital camera connected to the computer and focused on the material through a light microscope so as to be microscopically enlarged.

4. The method of claim 3 wherein the microscope is selected from the group consisting of microscopes utilizing phase contrast, confocal, laser, electron or atomic force imaging.

5. The method of claim 2 wherein a visual image of the material is scanned.

6. The method of claim 1 wherein in step (b) the range of grey level values is from 0 to 255.

7. The method of claim 1 wherein in step (d) the perimeter surface is determined by means of x and y coordinates of pairs of the pixels with maximum differences in the grey level values.

8. The method of claim 7 wherein the fractal dimension is found by using a box counting algorithm.

9. The method of claim 1 wherein in step (d) there are several different materials, a histogram based upon a ratio of a number of the material with a particular fractal dimension to a number of all of the materials versus the fractal dimension is developed for all materials within a sample by repeating the method for each material in the sample.

10. The method of claim 1 wherein in step (f) material which is identified or classified is diagnostically relevant.

11. The method of claim 10 wherein the material which is identified in step (f) is a malignant cell.

12. The method of claim 1 wherein the material which is identified is a cell.

13. The method of claim 1 wherein in step (a) the digital image is derived by digitizing a view of the material; wherein in step (d) the perimeter surface is determined by means of x and y coordinates of pairs of the pixels with maximum differences in the grey level values; wherein the fractal dimensions is found by using a box counting algorithm of the cell.

14. The method of claim 1 wherein a computer program controls the computer to perform steps (a) to (e).

15. The method of claim 14 wherein the program is as set forth in Appendix I.

16. The method of claim 1 wherein the steps (a) to (f) are each performed by an operator of the computer.

17. A system for identifying biological materials having a particle size between about 0.1 and 100 microns including parts thereof which comprises:

(a) a microscope adapted to view a sample containing the material; and (b) a digital means mounted on the microscope and connected to the computer to download a digital image of the material so that the program can perform a method which comprises providing a digitized image defined by pixels of a material in a memory of a computer with a range of grey level values and including small sized artifacts in and around the material; representing the range of grey level values in binary form using a minimum grey level value determined by a distribution of the grey level values of the pixels; removing the artifacts by eliminating general clusters of pixels of a minimum number; determining a perimeter surface of the material to be measured; measuring a fractal dimension of the perimeter surface of the material wherein by plotting log N(l) versus l, where N(l) is a number of boxes intersected by a surface of the material and l is a resolution representing a number of the boxes and wherein fractal dimension is a straight line slope of the plot where l is at least between 3 and 7; and identifying or classifying the material based upon the fractal dimension.

18. The system of claim 17 wherein in the computer the range of grey level values is from 0 to 255.

19. The system of claim 17 wherein in the computer the perimeter surface is determined by means of x and y coordinates of pairs of the pixels with maximum differences in the grey level values.

20. The system of claim 17 wherein in the computer the material which is identified or classified is diagnostically relevant.

21. The system of claim 17 wherein in the computer the material which is identified is a malignant cell.

22. The system of claim 17 wherein in the computer the grey level value is from 0 to 255; wherein the perimeter surface is determined by means of x and y coordinates of pairs of the pixels with maximum differences in the grey level value; wherein the fractal dimensions are found by using a box counting algorithm.

23. The system of claim 22 wherein the computer program produces a histogram of several different materials based upon a ratio of a number of the material with a particular fractal dimension to a number of all of the materials versus the fractal dimension is developed for all of the materials within a sample by repeating the method for each material in the sample.

24. The system of claim 23 wherein the histogram determines whether the material is a malignant cell.

25. In a method for identifying a cell having a size between about 0.1 and 100 microns which is diagnostically relevant, the improvement which comprises microscopically enlarging and then analyzing a fractal dimension of the cell and determining whether the cell is diagnostically relevant based upon the fractal dimension, wherein the fractal dimension is measured by plotting log N(l) versus l, where N(l) is a number of boxes intersected by a surface of the material and l is a resolution representing a number of the boxes and wherein fractal dimension is a straight line slope of the plot where l is at least between 3 and 7.

26. The method of claim 25 wherein the cell can be malignant.

27. The method of claim 26 wherein the cell is a blood cell.

28. The method of claim 27 wherein the cell is hairy cell leukemia.

* * * * *